United States Patent
Fujimoto et al.

(10) Patent No.: US 10,463,230 B2
(45) Date of Patent: Nov. 5, 2019

(54) ENDOSCOPE SYSTEM WITH POWER SUPPLY SYSTEM

(71) Applicant: OLYMPUS CORPORATION, Hachioji-shi, Tokyo (JP)

(72) Inventors: Takehide Fujimoto, Nishitama-gun (JP); Nanako Ubayama, Hachioji (JP); Hitoshi Komine, Hachioji (JP); Yutaka Fujisawa, Akishima (JP); Hideki Kato, Kokubunji (JP); Sadaaki Tomura, Kawaguchi (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/712,950

(22) Filed: Sep. 22, 2017

(65) Prior Publication Data

US 2018/0008124 A1 Jan. 11, 2018

Related U.S. Application Data

(63) Continuation of application No. PCT/JP2016/068716, filed on Jun. 23, 2016.

(30) Foreign Application Priority Data

Jun. 26, 2015 (JP) ................. 2015-128547

(51) Int. Cl.
*A61B 1/00* (2006.01)
*A61B 1/05* (2006.01)
*G02B 23/24* (2006.01)

(52) U.S. Cl.
CPC ...... *A61B 1/00027* (2013.01); *A61B 1/00059* (2013.01); *A61B 1/05* (2013.01); *G02B 23/2484* (2013.01); *G02B 23/2407* (2013.01)

(58) Field of Classification Search
CPC ............. A61B 1/00006; A61B 1/0002; A61B 1/00025; A61B 1/00027; A61B 1/00032;
(Continued)

(56) References Cited

U.S. PATENT DOCUMENTS 4,559,928 A * 12/1985 Takayama ............ A61B 1/0052
  388/838
5,966,425 A * 10/1999 Beland ................ H02M 7/1557
  378/108
(Continued)

FOREIGN PATENT DOCUMENTS

CN 104782040 A 7/2015
JP H08-37302 A 2/1996
(Continued)

OTHER PUBLICATIONS

Jan. 4, 2018 Translation of IPRP with Written Opinion issued in International Application No. PCT/JP2016/068716.
(Continued)

*Primary Examiner* — Timothy J Neal
*Assistant Examiner* — William B Chou
(74) *Attorney, Agent, or Firm* — Oliff PLC

(57) ABSTRACT

An endoscope power supply system includes an endoscope including an imaging unit that images an object, a housing apparatus to which the endoscope is detachably connected, a plurality of power source units that are provided in the housing apparatus and configured to output electric power different from one another, switches each provided in an output stage of each of the power source units of the housing apparatus and formed of two FETs that are back-to-back connected, and a controller that is provided in the housing apparatus, selects a power source unit necessary to operate the endoscope from the power source units, and controls the
(Continued)

switches to output electric power generated by the selected power source unit to the endoscope.

8 Claims, 4 Drawing Sheets

(58) Field of Classification Search
    CPC .......... A61B 1/00034; A61B 1/00059; A61B 1/00112; A61B 1/00121; A61B 1/00124; A61B 1/05; G02B 23/2484
    USPC ................ 600/109, 118, 132, 160, 180
    See application file for complete search history.

(56) References Cited

U.S. PATENT DOCUMENTS

| | | |
|---|---|---|
| 2004/0217653 A1 | 11/2004 | Neidorff |
| 2009/0209818 A1 | 8/2009 | Higuchi |
| 2009/0251068 A1* | 10/2009 | Holec ................ F21V 23/005 315/294 |
| 2011/0248632 A1 | 10/2011 | Williams et al. |
| 2012/0184814 A1 | 7/2012 | Ebata et al. |
| 2014/0043875 A1* | 2/2014 | Hsing ...................... G05F 1/56 363/77 |
| 2014/0275783 A1* | 9/2014 | Blanquart .......... A61B 1/00124 600/112 |
| 2015/0280550 A1* | 10/2015 | Minakuchi ......... A61B 1/00027 348/65 |
| 2015/0374204 A1* | 12/2015 | Tabuchi .................. A61B 1/04 600/109 |

FOREIGN PATENT DOCUMENTS

| | | |
|---|---|---|
| JP | H11-330410 A | 11/1999 |
| JP | 2008-259202 A | 10/2008 |
| JP | 2010-66409 A | 3/2010 |
| JP | 2014-162423 A | 9/2014 |
| WO | 2014/028866 A2 | 2/2014 |
| WO | 2015/019903 A1 | 2/2015 |

OTHER PUBLICATIONS

Aug. 2, 2018 Office Action issued in Chinese Patent Application No. 201680016307.8.
Aug. 30, 2016 International Search Report issued in International Patent Application No. PCT/JP2016/068716.
Jan. 31, 2017 Office Action issued in Japanese Patent Application No. 2016-564344.
Mar. 11, 2019 Extended European Search Report issued in European Patent Application No. 16814454.1.

* cited by examiner

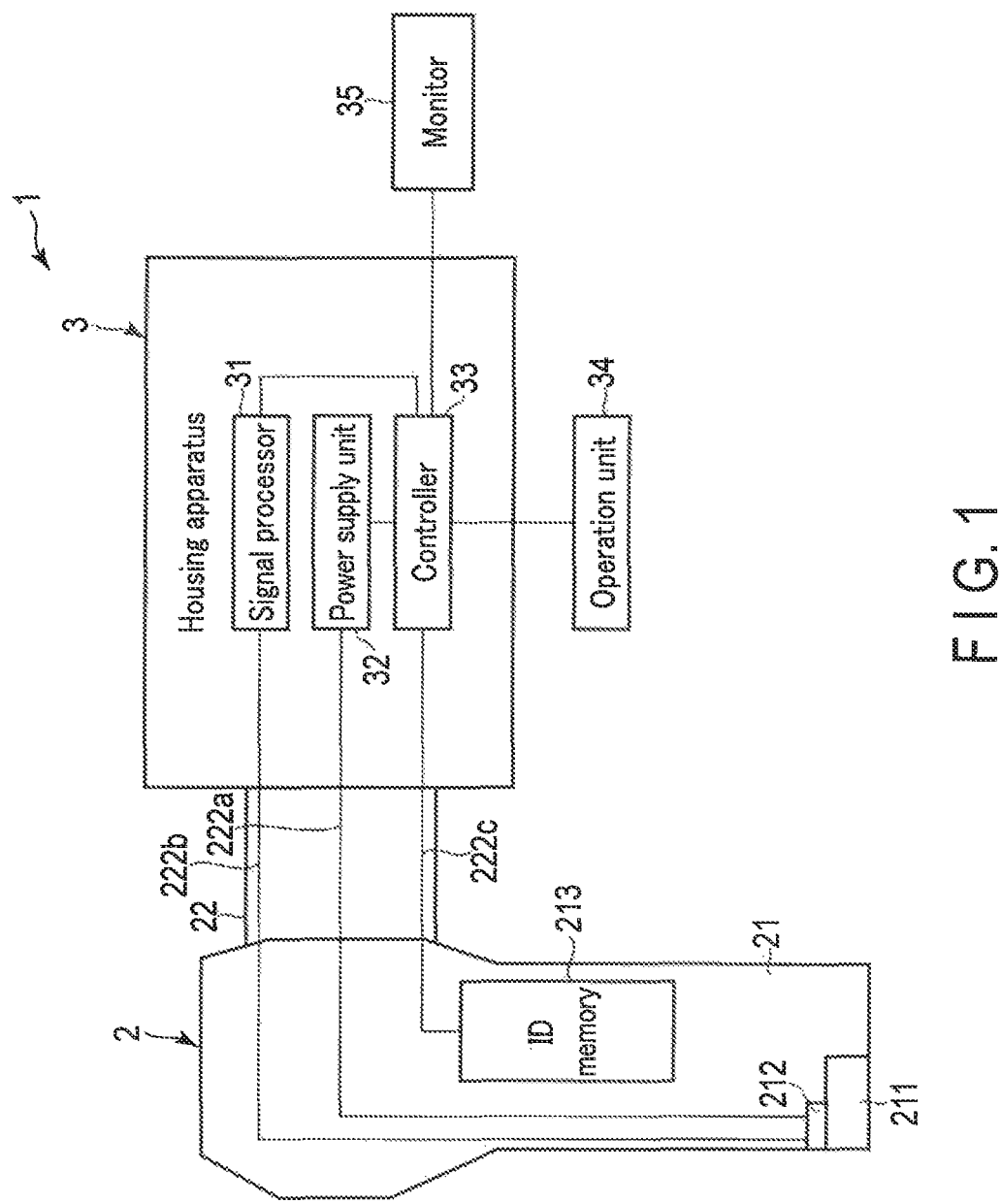
F I G. 1

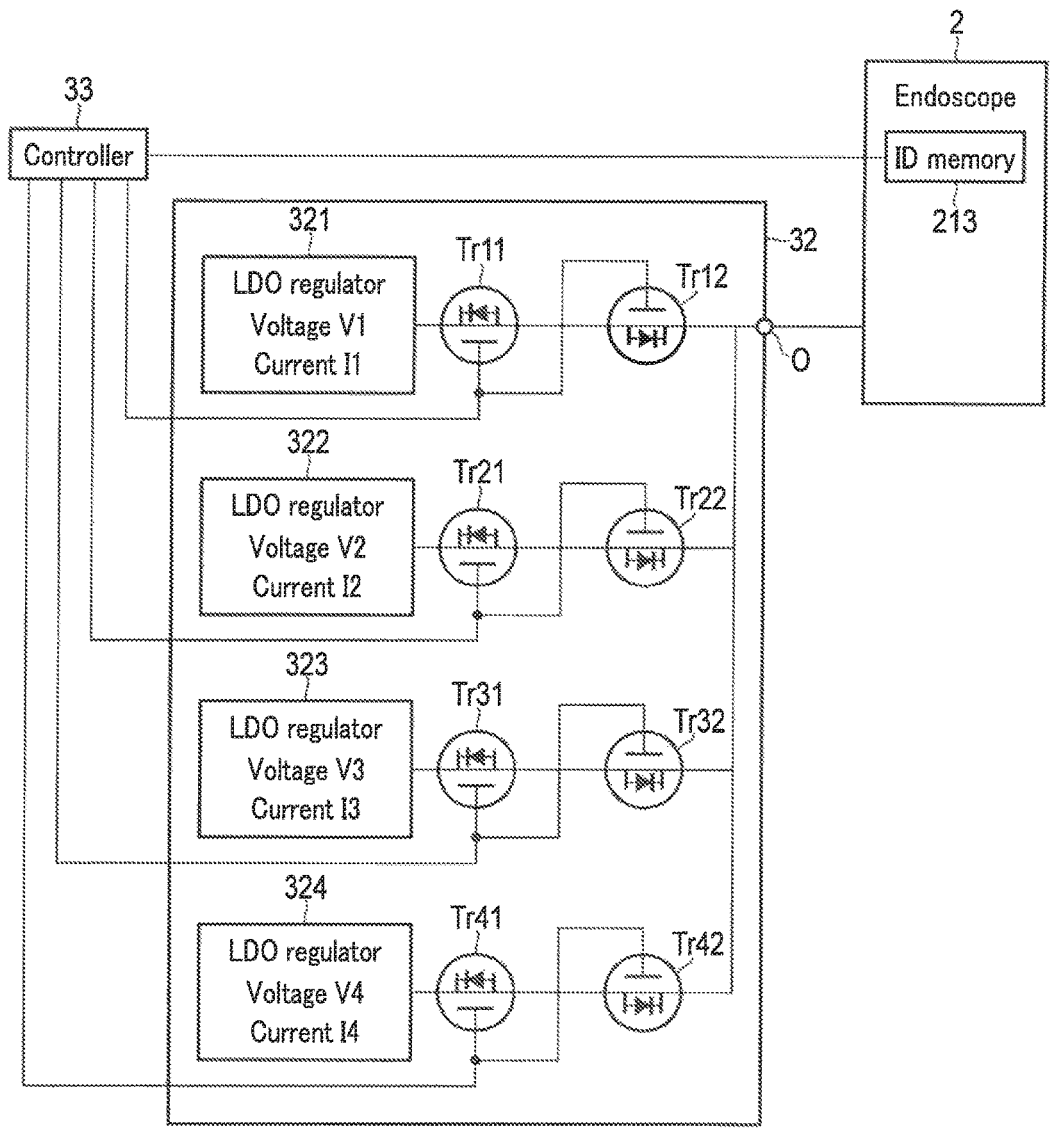
F I G. 2

US 10,463,230 B2

ENDOSCOPE SYSTEM WITH POWER SUPPLY SYSTEM

CROSS-REFERENCE TO RELATED APPLICATIONS

This application is a Continuation Application of PCT Application No. PCT/JP2016/068716, filed Jun. 23, 2016 and based upon and claiming the benefit of priority from the prior Japanese Patent Application No, 2015-128547, filed Jun. 26, 2015, the entire contents of both of which are incorporated herein by reference.

BACKGROUND OF THE INVENTION

1. Field of the Invention

The present invention relates to an endoscope power supply system.

2. Description of the Related Art

An endoscope system includes an endoscope and a housing apparatus to which the endoscope is attached. An endoscope in recent years incorporates various electronic elements corresponding to intended uses. The electronic elements incorporated in the endoscope are operated upon receipt of power supplied from the housing apparatus. In endoscope power supply systems proposed in recent years, a magnitude of electric power output from a power source unit of the housing apparatus is variable, so that the system can cope with reduction in voltage due to aging degradation in the endoscope or can be adapted to various types of endoscope in accordance with intended uses. For example, Jpn. Pat. Appln. KOKAI Publication No, 2010-66409 discloses an endoscope apparatus in which a magnitude of electric power supplied to an endoscope is determined in accordance with an ID of an insertion section and an ID of a cable of the endoscope.

BRIEF SUMMARY OF THE INVENTION

An endoscope power supply system according to an aspect of the invention comprises: an endoscope including an imaging unit that images an object; a housing apparatus to which the endoscope is detachably connected; a plurality of power source units that are provided in the housing apparatus and configured to output electric power different from one another; switches, each provided in an output stage of each of the power source units of the housing apparatus and formed of two FETs that are back-to-back connected; and a controller that is provided in the housing apparatus, selects a power source unit necessary to operate the endoscope the power source units, and controls the switches to output electric power generated by the selected power source unit to the endoscope.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing a configuration of an endoscope power supply system according to a first embodiment of the present invention.

FIG. 2 is a diagram showing a configuration relating to power output to an endoscope in a power supply unit of the first embodiment.

DETAILED DESCRIPTION OF THE INVENTION

Figure 3:
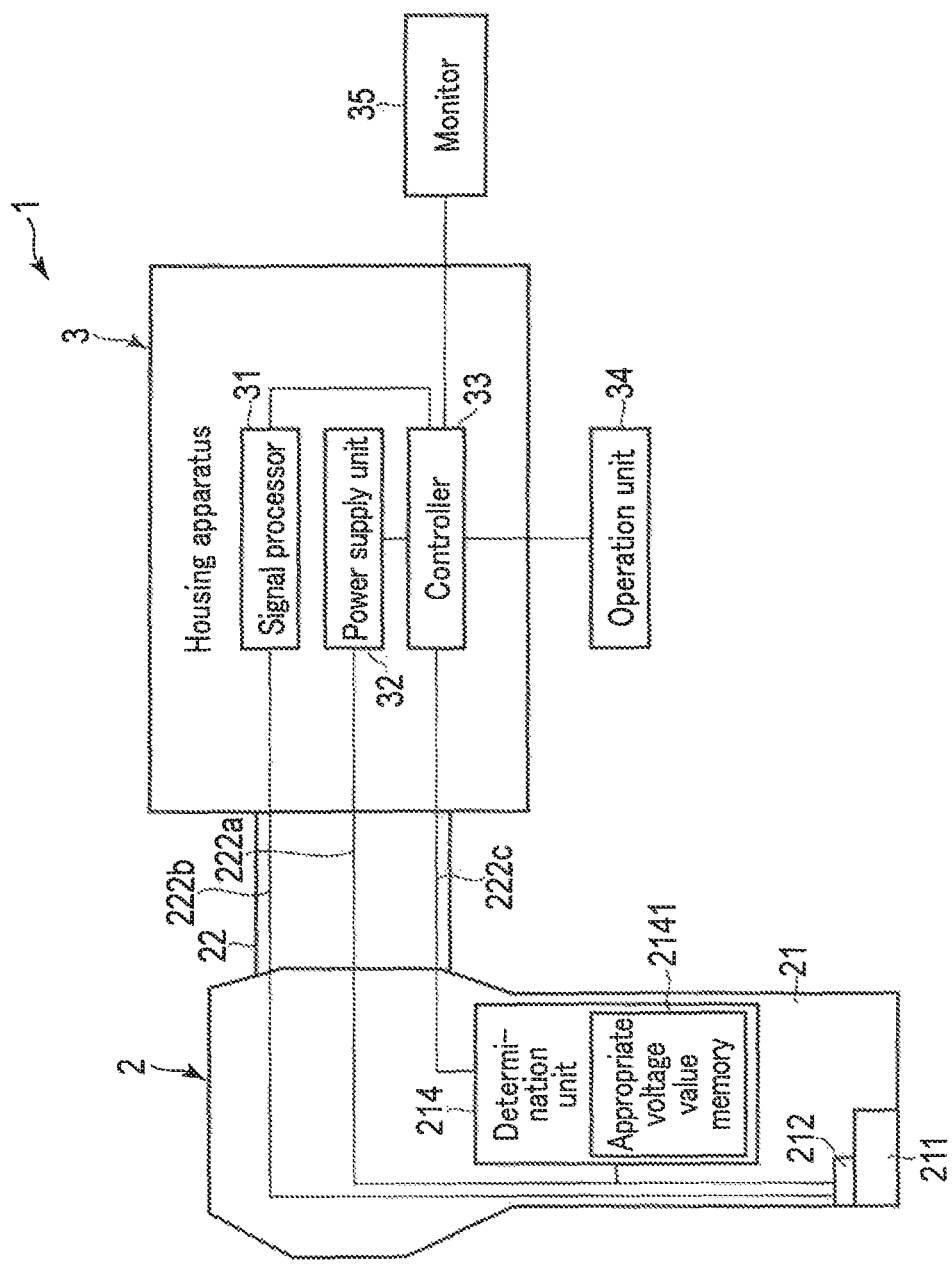
FIG. 3 is a block diagram showing a configuration of an endoscope power supply system according to a second embodiment of the present invention.

Embodiments of the present invention will be described with reference to the accompanying drawings.

First Embodiment

The first embodiment of the present invention is explained below. FIG. 1 is a block diagram showing a configuration of an endoscope power supply system according to a first embodiment of the present invention. The endoscope power supply system 1 includes an endoscope 2 and a housing apparatus 3. The endoscope 2 includes an imaging unit to observe an inside of a subject body, which is an object to be imaged. The housing apparatus 3 outputs power to actuate electronic elements incorporated in the endoscope 2. In the following, blocks in the endoscope power supply system 1 will be explained.

The endoscope 2 includes an insertion section 21 and a cable 22. The insertion section 21 is a scope portion of the endoscope 2 and is inserted in the subject body. An objective lens 211 and an imaging element 212 are provided at a distal end of the insertion section 21. The objective lens 211 is an optical system to form an image received from the object on the imaging element 212. The imaging element 212, which constitutes the imaging unit together with the objective lens 211, is one of the electronic elements incorporated in the endoscope 2. The imaging element 212 includes pixels arranged two dimensionally. Each of the pixels is, for example, a photodiode, and generates an electric signal (image signal) corresponding to the amount of light input through the objective lens 211.

The endoscope 2 also includes an ID memory 213. The ID memory 213 is, for example, a flash memory, and stores ID information indicative of a type of the endoscope 2.

The cable 22 is connected to the housing apparatus 3 via a connector (not shown). In the cable 22, a power supply line 222a, an output signal line 222b, and a communication line 222c are contained. The power supply line 222a is connected to the imaging element 212, and is configured to be connected to a power supply unit 32 of the housing apparatus 3, when the insertion section 21 is connected to the housing apparatus 3 via the connector (not shown). The power supply line 222a is a signal line to supply electric power generated in the housing apparatus 3 to the imaging element 212. The output signal line 222b is connected to the imaging element 212, and is configured to be connected to a signal processor 31 of the housing apparatus 3, when the insertion section 21 is connected to the housing apparatus 3 via the connector (not shown). The output signal line 222b is a signal line to transmit an image signal generated in the imaging element 212 to the signal processor 31. The communication line 222c is connected to the ID memory 213, and is configured to be connected to a controller 33 of the housing apparatus 3, when the insertion section 21 is connected to the housing apparatus 3 via the connector (not shown). The communication line 222c is a signal line to communicate information such as the ID information.

The housing apparatus 3 is configured so as to detachably connect the endoscope 2, and executes processing such as control of the endoscope 2. For example, the housing apparatus 3 is a video processor that processes an image signal generated by the endoscope 2. In this case, the housing apparatus 3 includes the signal processor 31, the power supply unit 32, and the controller 33. Outside the housing apparatus 3, an operation unit 34 is provided. The housing apparatus 3 is connected to a monitor 35.

The signal processor 31 executes various types of signal processing for the image signal from the imaging element 212. For example, the signal processor 31 executes signal processing to correct luminance characteristics and chromatic characteristics of the image signal to be adapted to a display in the monitor 35.

The power supply unit 32 outputs power to actuate electronic elements incorporated in the housing apparatus 3 and electronic elements incorporated in the endoscope 2. Details of the power supply unit 32 are described later.

The controller 33 is formed of, for example, an FPGA (Field Programmable Gate Array) and controls operations of the housing apparatus 3. The controller 33 also reads the ID information of the endoscope 2 from the ID memory 213 of the endoscope 2, and performs a control specific to the endoscope 2 in accordance with the read ID information. The control includes power management of the endoscope 2.

The operation unit 34 includes an operation member to allow a user to operate the housing apparatus 3. The operation member may be of a type such as a button or a switch, or a type such as a touch panel. When the operation member of the operation unit 34 is operated, the controller 33 controls various types of processing in accordance with the operation of the operation unit 34.

The monitor 35 is, for example, a liquid crystal display. The monitor 35 displays an image and the like generated as a result of signal processing by the signal processor 31 under the control of the controller 33.

The power supply unit 32 is explained below. FIG. 2 is a diagram showing a configuration relating to power output to the endoscope 2 in the power supply unit 32 of the first embodiment. The power supply unit 32 includes a plurality of LDO regulators (Low Dropout regulators), which are power source units. In the example shown in FIG. 2, the power supply unit 32 includes four LDO regulators 321, 322, 323, and 324.

Each of the LDO regulators of this embodiment is a fixed voltage output LDO regulator, which outputs a predetermined fixed voltage. The LDO regulator 321 converts an input voltage to a voltage V1 and outputs the voltage V1. A current output from the LDO regulator 321 is I1. The LDO regulator 322 converts an input voltage to a voltage V2 and outputs the voltage V2. A current output from the LDO regulator 322 is I2. The LDO regulator 323 converts an input voltage to a voltage V3 and outputs the voltage V3. A current output from the LDO regulator 323 is I3. The LDO regulator 324 converts an input voltage to a voltage V4 and outputs the voltage V4. A current output from the LDO regulator 324 is I4. The values of the voltages V1, V2, V3, and V4 are different from one another. The values of the currents I1, I2, I3, and I4 may be different or the same.

An output stage of the LDO regulator 321 is connected to a switch including two FETs, namely FET Tr11 and FET Tr12, which are back-to-back connected. Back-to-back connection is a connection structure in which the same terminals of the two FETs are connected. For example, a drain of the FET Tr11 is connected to the output stage of the LDO regulator 321, and a source of the FET Tr11 is connected to a source of the FET Tr 12. A drain of the FET Tr12 is connected to an output terminal O of the power supply unit 32. Furthermore, gates of the FET Tr11 and the FET Tr12 are connected to the controller 33. In the back-to-back connection described above, the directions of body diodes of the FET Tr11 and the FET Tr12 are opposite to each other.

Similarly, an output stage of the LDO regulator 322 is connected to two FETs, namely FET Tr21 and FET Tr22, which are back-to-back connected, and an output stage of the LDO regulator 323 is connected to two FETs, namely FET Tr31 and FET Tr32, which are back-to-back connected. An output stage of the LDO regulator 324 is connected to two FETs, namely FET Tr41 and FET Tr42, which are back-to-back connected. The connection structure of each of the pair of the FET Tr21 and the FET Tr22, the pair of the FET Tr31 and the FET Tr32, and the pair of the FET Tr41 and the FET Tr42 is the same as that of the pair of the FET Tr11 and the FET Tr12.

Operations of the endoscope power supply system 1 of this embodiment will be explained. For example, when the user turns on the power source of the operation unit 34 of the housing apparatus 3, the endoscope power supply system 1 starts operating. When the housing apparatus 3 is powered on, the controller 33 reads the ID information of the endoscope 2 from the ID memory 213 through the communication line 222c. The controller 33 determines the type of the endoscope 2 from the read ID information, and controls switches in accordance with the type.

In this embodiment, depending on the type of the endoscope 2, the endoscope 2 is associated with the LDO regulator that is necessary to operate the endoscope 2. The controller 3 controls the switches in accordance with the association. For example, if the controller 33 determines that the LDO regulator necessary to operate the endoscope 2 is the LDO regulator 321 in view of the type of the endoscope 2 determined from the ID information, the controller 33 applies a gate-on voltage to the gates of the FET Tr11 and the FET Tr12. As a result, the voltage V1 and the current I1 (power P1) generated by the LDO regulator 321 are output to the endoscope 2 through the power supply line 222a. The electronic element, for example, the imaging element 212, of the endoscope 2 is actuated by the power P1.

In the example described above, one LDO regulator is selected for one endoscope 2. However, the embodiment may be configured so that two or more LDO regulators are selected for one endoscope 2. For example, if the controller 33 determines that the LDO regulators necessary to operate the endoscope 2 are the LDO regulator 321 and the LDO regulator 322 in view of the type of the endoscope 2 determined from the ID information, the controller 33 applies a gate-on voltage to the gates of the FET Tr11 and the FET Tr12 and the gates of the FET Tr21 and the FET Tr22.

The imaging element 212 images an inside of the subject body and generates an image signal concerning the subject body. The image signal generated by the imaging element 212 is input to the signal processor 31 of the housing apparatus 3 through the output signal line 222b. The signal processor 31 executes signal processing for the image signal. Thereafter, the controller 33 inputs to the monitor 35 an image generated as a result of the signal processing of the signal processor 31, and causes the monitor 35 to start displaying the image.

Accordingly, the image inside the subject body is displayed on the monitor 35.

As described above, according to this embodiment, the power supply unit 32 of the housing apparatus 3 includes a plurality of power supply units respectively associated with the types of the endoscope 2, not a single power supply unit. Accordingly, the housing apparatus 3 can output power suitable for the respective types of the endoscope 2 that need different magnitudes of power to actuate. Furthermore, since the power source units are provided for the respective types of the endoscope 2, a power source unit for a variable voltage output is not required. Therefore, the difference between an input voltage and an output voltage in the power source unit can be small, so that needless heat generation can be suppressed.

Besides, in this embodiment, two FETs which are back-to-back connected are used to switch between outputs of the power source units. FETs are inexpensive as compared to relays. In a switch using a single FET, when a current flows through the FET, the current also flows to another power source unit through a body diode of another FET. In contrast, the present embodiment uses a switch formed of two FETs which are back-to-back connected. Because of the use of two back-to-back connected FETs, a backward current cannot flow to another power source unit, unlike in the case of using a single FET.

Furthermore, since a flow of a backward current is prevented, outputs from a plurality of power source units can pass through one power supply line 222a in common.

In the embodiment described above, the type of the endoscope 2 can be determined by reading of the ID information from the ID memory 213. However, the method of determination by the endoscope 2 is not limited to reading of the ID information. For example, the endoscope 2 may include a resistor having a resistance value that is specific to the type of the endoscope, and the housing apparatus 3 may be configured to read the resistance value. With this configuration, the type of the endoscope 2 can be determined by reading the resistance value instead of reading the ID information from the ID memory 213.

Furthermore, in this embodiment, since it is only necessary to discriminate the type of the imaging element to which power is supplied, the ID information stored in the ID memory 213 may be information indicative of only the type of the imaging element provided in the endoscope 2. Alternatively, in the case of reading the resistance value as described above, the resistance value may be information indicative of only the type of the imaging element.

Second Embodiment

The second embodiment of the present invention is explained below. FIG. 3 is a block diagram showing a configuration of an endoscope power supply system according to the second embodiment of the present invention. As in the first embodiment, an endoscope power supply system of the second embodiment includes an endoscope 2 and a housing apparatus 3. In the following, blocks in the endoscope power supply system 1 will be explained. In FIG. 3, blocks that are the same as those shown in FIG. 1 are specified by the same reference symbols as those in FIG. 1, and explanations thereof are omitted.

An insertion section 21 of the endoscope 2 of the second embodiment includes a determination unit 214 instead of the ID memory 213. The determination unit 214 includes an appropriate voltage value memory 2141. The appropriate voltage value memory 2141 is, for example, a flash memory, and stores information indicative of an appropriate voltage value (or a range thereof) necessary to operate the endoscope 2. The determination unit 214 is connected to a power supply line 222a. In this configuration, the determination unit 214 digitizes and takes in a voltage output from a power supply unit 32 of the housing apparatus 3 and applied to the endoscope 2, and compares a value of the taken-in voltage with the appropriate voltage value stored in the appropriate voltage value memory 2141. If a difference between the value of the taken-in voltage and the appropriate voltage value stored in the appropriate voltage value memory 2141 exceeds a predetermined value, the determination unit 214 requests the housing apparatus 3 through the communication line 222c to output the appropriate voltage.

The controller 33 is formed of, for example, FPGA (Field Programmable Gate Array) and controls operations of the housing apparatus 3. The controller 33 also carries out power management of the endoscope 2 in accordance with a request from the determination unit 214.

Figure 4:
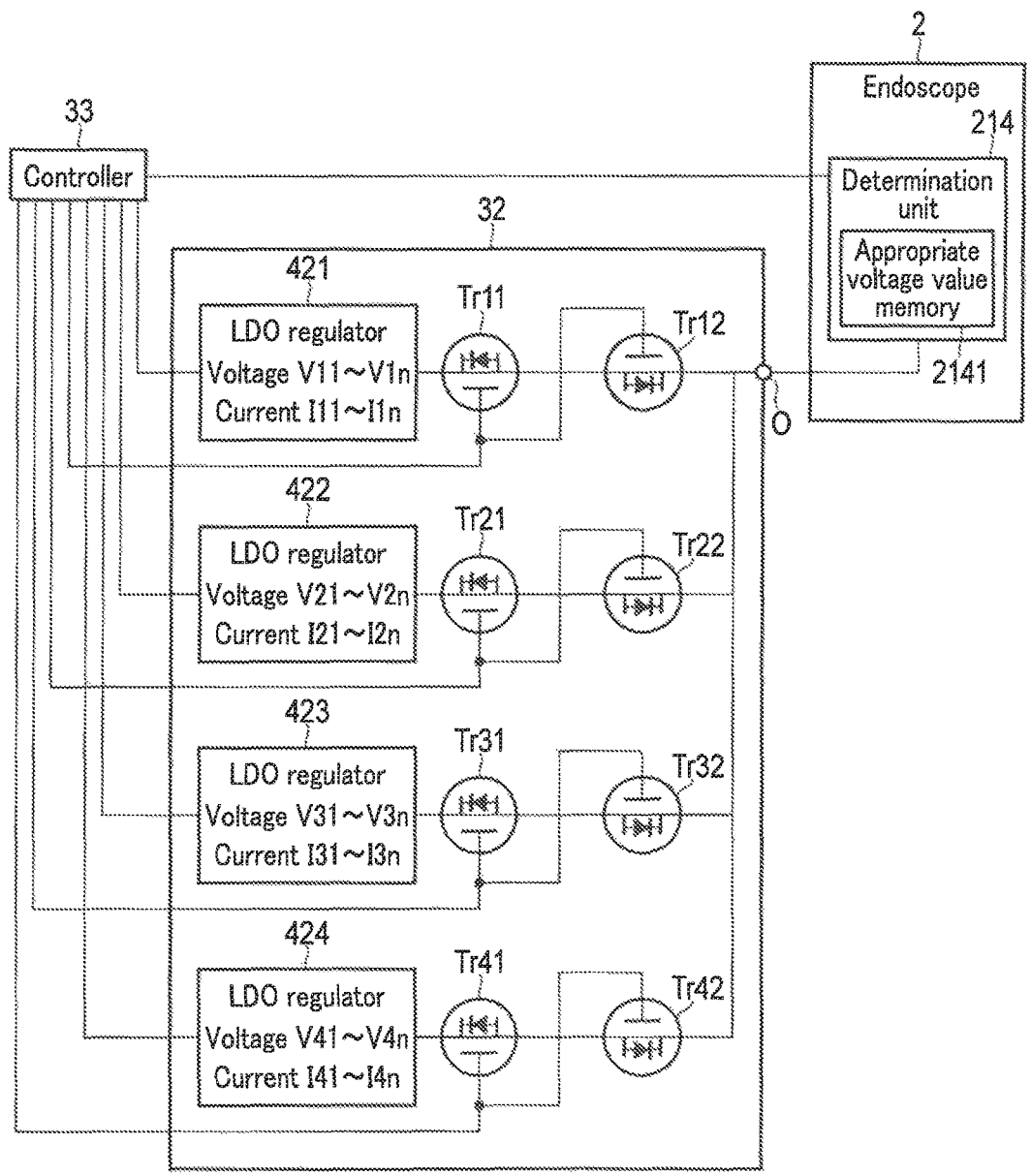
FIG. 4 is a diagram showing a configuration relating to power output to an endoscope in a power supply unit of the second embodiment.

The power supply unit 32 is explained below. FIG. 4 is a diagram showing a configuration relating to power output to the endoscope 2 in the power supply unit 32 of the second embodiment. The power supply unit 32 of the second embodiment also includes a plurality of LDO regulators, which are power source units. In the example shown in FIG. 4, the power supply unit 32 includes four LDO regulators 421, 422, 423, and 424.

Each of the LDO regulators of this embodiment is a variable voltage output LDO regulator, which outputs a variable voltage. The LDO regulator 421 converts an input voltage to a voltage in a range from $V11$ to $V1n$ and outputs the converted voltage. A current output from the LDO regulator 421 is a current in a range from $I11$ to $I1n$. The LDO regulator 422 converts an input voltage to a voltage in a range from $V21$ to $V2n$ and outputs the converted voltage. A current output from the LDO regulator 422 is a current in a range from $I21$ to $I2n$. The LDO regulator 423 converts an input voltage to a voltage in a range from $V31$ to $V3n$ and outputs the converted voltage. A current output from the LDO regulator 423 is a current in a range from $I31$ to $I3n$. The LDO regulator 424 converts an input voltage to a voltage in a range from $V41$ to $V4n$ and outputs the converted voltage. A current output from the LDO regulator 424 current in a range from $I41$ to $I4n$. Voltage ranges from $V11$ to $V1n$, from $V21$ to $V2n$, from $V31$ to $V3n$, and from $V41$ to $V4n$ are different from one another. However, parts of the ranges may overlap. Current ranges from $I11$ to $I1n$, from $I21$ to $I2n$, from $I31$ to $I3n$, and from $I41$ to $I4n$ may be either different or the same.

In the second embodiment, as in the first embodiment, an output stage of the LDO regulator 421 is connected to a switch including two FETs, namely FET Tr11 and FET Tr12, which are back-to-back connected. Similarly, an output stage of the LDO regulator 422 is connected to two FETs, namely FET Tr21 and FET Tr22, which are back-to-back connected. An output stage of the LDO regulator 423 is connected to two FETs, namely FET Tr31 and FET Tr32, which are back-to-back connected. An output stage of the LDO regulator 424 is connected to two FETs, namely FET Tr41 and FET Tr42, which are back-to-back connected.

Operations of the endoscope power supply system 1 of this embodiment will be explained. For example, when the user turns on the power source of the operation unit 34 of the housing apparatus 3, the operations of the endoscope power supply system 1 start. When the housing apparatus 3 is powered on, the determination unit 214 of the endoscope 2 requests the controller 33 of the housing apparatus 3 through the communication line 222c to output electric power corresponding to the appropriate voltage value. The controller 33 controls the switches so that the appropriate voltage value in accordance with the request is output from the power supply unit 32. For example, if the requested appropriate voltage value falls within the voltage range of the LDO regulator 421, the controller 33 applies a gate-on voltage to the gates of the FET Tr11 and the FET Tr12. Furthermore, the controller 33 executes setting to cause the LDO regulator 421 to output an output voltage that is the requested appropriate voltage. For this purpose, the controller 33 inputs, for example, an analog voltage indicative of the appropriate voltage to the LDO regulator 421. As a result, the voltage and the current generated by the LDO regulator 421 are output to the endoscope 2 through the power supply line 222a. The electronic element, for example, the imaging element 212, of the endoscope 2 is actuated by the electric power.

In the example described above, one LDO regulator is selected for one endoscope 2. However, the embodiment may be configured so that two or more TOO regulators are selected for one endoscope 2.

The imaging element 212 images an inside of the subject body and generates an image signal concerning the subject body. The image signal generated by the imaging element 212 is input to the signal processor 31 of the housing apparatus 3 through the output signal line 222b. The signal processor 31 executes signal processing for the image signal. Thereafter, the controller 33 inputs to the monitor 35 an image generated as a result of the signal processing of the signal processor 31, and causes the monitor 35 to start displaying the image. Accordingly, the image inside the subject body is displayed on the monitor 35.

During operations of the endoscope 2, the determination unit 214 digitizes and takes in a voltage output from a power supply unit 32 of the housing apparatus 3 and applied to the endoscope 2, and compares a value of the taken-in voltage with the appropriate voltage value stored in the appropriate voltage value memory 2141. If a difference between the value of the taken-in voltage and the appropriate voltage value stored in the appropriate voltage value memory 2141 exceeds a predetermined value, the determination unit 214 requests the housing apparatus 3 through the communication line 222c to output the appropriate voltage.

The controller 33 controls the switches so that the appropriate voltage value in accordance with the request is output from the power supply unit 32. For example, if the voltage applied to the endoscope 2 is lower than the appropriate voltage value because of an increase in resistance due to aging degradation of the cable 22, the controller 33 executes controlling to increase the voltage output from the power supply unit 32. For example, if the difference between the voltage applied to the endoscope 2 and the appropriate voltage value falls within a range of voltage that can be generated by the LDO regulator 421, the controller 33 sets the LDO regulator 421 to increase the output voltage by the difference. On the other hand, if the difference between the voltage applied to the endoscope 2 and the appropriate voltage value does not fall within a range of voltage that can be generated by the LDO regulator 421, the controller 33 controls the switches to select another LDO regulator.

As described above, the second embodiment achieves the same advantageous effects as those of the first embodiment. Furthermore, in the second embodiment, the applied voltage is monitored in the endoscope 2. If the value of the applied voltage is not the appropriate voltage value, the endoscope 2 requests the housing apparatus 3 to output the appropriate voltage. As a result, even if a voltage drop occurs due to aging degradation of the endoscope 2 or the like, the appropriate voltage can be applied to the endoscope 2.

In the second embodiment, the applied voltage is monitored. Instead, however, the embodiment may be configured so that both a voltage and a current are detected to monitor whether or not the electric power supplied to the endoscope 2 is appropriate electric power.

Although the present invention has been described based on the embodiments, the invention is not limited to these embodiments, and various modifications or applications may be made without departing from the spirit or scope of the general inventive concept of the present invention.

For example, in the above embodiments, the endoscope 2 is a type of endoscope that forms an image to observe an object with an imaging element. However, the "endoscope" of the embodiments is not limited to such a configuration. The "endoscope" of the embodiments may be of any type that contains an electronic element therein. For example, an optical endoscope (optical viewing tube or fiber scope) may be included in the "endoscope" of the present invention, if it has a configuration in which a camera scope can be connected to an eyepiece. Furthermore, the "endoscope" of the embodiments includes both a soft endoscope and a hard endoscope. Moreover, the electronic element is not limited to an imaging element.

In the embodiments described above, the housing apparatus 3 is a video processor. However, the housing apparatus 3 is not limited to a video processor. For example, the housing apparatus 3 may be a light source apparatus that supplies illumination light to the endoscope 2. The housing apparatus 3 may integrally include both a video processor and a light source apparatus.

In the embodiments described above, the power supply unit is an LDO regulator. However, the power supply unit is not limited to an LDO regulator. For example, the power supply unit may be a DC-DC converter. However, the LDO regulator can reduce a ripple noise in comparison with the DC-DC converter.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
  a single endoscope including a camera that images an object, and a cable;
  a housing apparatus detachably connected to the single endoscope via the cable;
  a plurality of power source units that are provided in the housing apparatus and configured to output electric power different from one another;
  a plurality of switches, each provided in an output stage of each of the power source units of the housing apparatus and formed of a back-to-back connection in which identical terminals of the two FETs are connected;

a common power supply line that provides common electric power output through the switches in common within the housing apparatus, the common power supply being configured to supply the common electric power output to the single endoscope from the housing apparatus;

a first processor that is provided in the single endoscope, the first processor being programmed to determine whether or not the electric power supplied through the common power supply line is an appropriate electric power to operate the single endoscope;

a communication line through which the single endoscope requests the housing apparatus to output appropriate electric power, when the first processor determines that the electric power supplied through the common power supply line is not appropriate electric power to operate the single endoscope; and a second processor that is provided in the housing apparatus, the second processor being programmed to:
  select a power source unit from the power source units in accordance with a request for appropriate electric power input through the communication line, and
  control the switches to output electric power generated by the selected power source unit to the single endoscope.

2. The endoscope system according to claim 1, further comprising
  a memory that is provided in the single endoscope, the memory storing information specific to a type of the single endoscope,
  wherein the second processor selects the power source unit for outputting electric power to operate the single endoscope from the power source units in accordance with the information specific to the type.

3. The endoscope system according to claim 2, wherein the information memory stores information indicative of a type of an imaging element that forms the imaging unit provided in the single endoscope.

4. The endoscope system according to claim 1,
  wherein the endoscope further includes a resistor having a resistance value that is specific to a type of the single endoscope; and
  wherein the housing apparatus reads the resistance value of the resistor, and selects the power source unit that is necessary to output electric power necessary to operate the single endoscope from the power source units in accordance with the read resistance value.

5. The endoscope system according to claim 4, wherein the resistor has a resistance value corresponding to a type of an imaging element that forms the camera provided in the single endoscope.

6. The endoscope system according to claim 1, wherein each of the power source units is a variable regulator.

7. The endoscope system according to claim 1, wherein each of the power source units is an LDO regulator.

8. The endoscope system according to claim 1, wherein the first processor is further programmed to:
  obtain a voltage supplied through the common power supply line,
  compare the voltage with a prestored appropriate voltage value, and
  request an output of appropriate electric power through the communication line, if a difference between the taken in voltage and the appropriate voltage value exceeds a predetermined value.

* * * * *